United States Patent [19]

Burroughs et al.

[11] Patent Number: 5,055,267
[45] Date of Patent: Oct. 8, 1991

[54] THIN FILM ENVIRONMENTAL MONITOR

[75] Inventors: G. Edward Burroughs, Lebanon; David J. Huebener, Ross, both of Ohio

[73] Assignee: The United States of America as represented by the Secretary of the Department of Health and Human Services, Washington, D.C.

[21] Appl. No.: 234,092

[22] Filed: Aug. 19, 1988

[51] Int. Cl.[5] .................................. G01N 21/25
[52] U.S. Cl. .................................. 422/83; 422/85; 422/87; 436/169
[58] Field of Search ............... 422/83, 85, 86, 87; 436/169

[56] References Cited

U.S. PATENT DOCUMENTS

| 3,114,610 | 12/1963 | Gafford et al. | 422/86 |
| 3,399,273 | 9/1968 | Grosskopf | 422/86 |
| 3,725,658 | 4/1973 | Stanley et al. | 422/83 |
| 3,853,477 | 12/1974 | Block et al. | 422/91 |
| 4,023,930 | 5/1977 | Blunck et al. | 422/87 |
| 4,125,372 | 11/1978 | Kawai et al. | 436/169 |
| 4,348,358 | 9/1982 | McKee et al. | 422/87 |
| 4,513,087 | 4/1985 | Giuliani et al. | 436/96 |
| 4,554,133 | 11/1985 | Leichnitz | 422/87 |
| 4,661,320 | 4/1987 | Ito et al. | 422/88 |
| 4,849,172 | 7/1989 | Yafuso et al. | 436/169 |

Primary Examiner—Robert J. Warden
Assistant Examiner—Lynn M. Kummert
Attorney, Agent, or Firm—Lowe, Price, LeBlanc & Becker

[57] ABSTRACT

A thin film environmental monitor for monitoring a person's exposure to an analyte in an environment, comprising a portable casing for housing the monitor, a pump in the casing for obtaining an air sample, and a sensor in the casing for sensing the concentration of the analyte in the air sample obtained by the pump. The sensor includes an active film portion coated with a dry coating adapted to cause a chemical reaction with the analyte, and a reference film portion for transmitting incident light independently of the concentration of analyte in the air sample. The sensor generates an active signal representing the amount of light transmitted by the active film portion and a reference signal representing the amount of light transmitted by the reference film portion. A control circuit is provided in the casing for providing voltage to the sensor and for processing the active and reference signals from the sensor and producing an output signal representative of the concentration of the analyte in the air sample. Indicators are provided connected to the casing responsive to the control circuit for indicating the amount of analyte sensed based on the representative output signal.

14 Claims, 12 Drawing Sheets

THIN FILM ENVIRONMENTAL MONITOR

BACKGROUND OF THE INVENTION

1. Field of the Invention

The present invention relates to public health and, more particularly, to monitoring a person's exposure to contaminants in the environment and a device for carrying out such monitoring.

2. The Prior Art

Prior techniques for monitoring exposure to environmental contaminants have been frequently limited to conventional sampling and analytical techniques for personal measurement or the use of bulky non-personal devices for determining contaminant concentration in general work environments.

In the case of ammonia, (a common environmental contaminant), current monitoring techniques include the following. NIOSH Method P&CAM 205 (NIOSH Manual of Analytical Methods, Second Ed., Vol. 1, Apr. 1977, NIOSH, CDC, PHS) requires that a sampler containing sulfuric acid be attached to the worker, with a 15 minute time weighted average exposure determined by subsequent laboratory analysis of the sample. NIOSH Method S347 (Ibid, Vol. 5) replaces the liquid acid with a solid sorbent tube, but extends the sampling period to approximately four hours, and still requires post-sampling laboratory analysis. Thus, neither of these methods allow for real-time determination of the safety of the worker.

The use of direct reading instrumental techniques, such as portable infrared analyzers, provide a real-time determination of ammonia concentration in the air, but it is seldom possible to determine the concentration of analyte in a person's breathing zone by this technique. Since this type of analyzer requires 110 VAC power and weighs approximately 50 pounds (depending on the model), it is not possible to follow a worker to various work stations, i.e., the device lacks reasonable portability. Therefore, only in those rare instances where an individual remains in one location is this a possible method for measuring personal exposure to contaminant, and even then there are significant limitations.

While these examples are specific to one environmental contaminant (ammonia), they are typical of the types of sampling required for other contaminants, including mercury, carbon monoxide, and formaldehyde.

A number of patents have been issued on devices which are designed to detect a change in some optical properties as a result of exposure of a sensor to a gas phase material. Thus, U.S. Pat. No. 3,114,610 to Gafford et al discloses a continuous sampling gas analyzer which uses a gel substance which contains a neutral liquid (water) which evaporates and gives the sensing gel a short life; this life is increased to some extent by the inclusion of a semi-permeable membrane, but even then the practical life of the device is limited. Further, this patent only covers gels which will change color due to changes in pH sensitive dye when it reacts with the analyte of interest, thus limiting the scope of use. Gafford's improved version of the device (shown in FIG. 2 of the patent) increases response time but uses two light sources, thus increasing its cost and complexity.

U.S. Pat. No. 3,853,477 to Block et al discloses a device for measuring only ethanol in discrete samples of air, for example breath. Block's device has both an active and reference side in the detector, however both sides use liquid reagent. While smaller in size than many laboratory instruments, its portability is nonetheless limited by its utilization of 110 VAC power.

U.S. Pat. No. 4,484,818 to Houston only covers oxygen detection using a barium metal film. The device also does not have a reference side to the detector, and thus is not nearly as sensitive as is physically possible. It does not measure analyte in the sense that it provides information on the amount present; rather it is an endpoint indicator providing evidence that a predetermined level has been obtained. The scientific principle on which this device is based precludes the possibility of using such a device to measure any analyte in an air matrix.

U.S. Pat. No. 4,513,087 to Giuliani et al covers only oxazine perchlorate reactions in an optical waveguide. Thus it is only sensitive to ammonia, hydrazine or pyridine, and the reaction is reversible (the color of the indicator will return to normal when the concentration of ammonia is zero) and leaves no permanent record of reaction. It also does not use a reference beam to detect and compensate for changes in the light source output.

U.S. No. 4,661,320 to Ito et al is for hydrogen only and specifically only for a detector which uses a "catalytic metal". The scientific principle on which this device is based precludes the possibility of using such a device to measure other analytes in air.

none of these patents provide a device which can monitor, in real time, the amount of contaminants in the environment to which a worker has been exposed.

SUMMARY OF THE INVENTION

Accordingly, it is an object of the present invention to overcome deficiencies in the prior art, such as indicated above.

it is another object of the present invention to improve the public health and more particularly to improve the monitoring of exposure to contaminants in the environment.

It is yet another object of the present invention to provide an improved de ice for the monitoring of exposure to contaminants in The environment.

it is still another object of the present invention to provide a thin film environmental monitor for real time and/or time history monitoring of a person's exposure to contaminants in the environment.

It is a further object of the present invention to provide a monitor which will monitor, in real time, the exposure levels of the worker wearing the monitor, to chemical contaminants in the environment. The sensor comprises an air sampling pump, a reagent coated slide which changes color upon exposure to the contaminant, and a calorimeter for electronically measuring the change in color. The calorimeter has a single light source and two light detectors, one for sampling the light passing through the reagent, and the other for measuring the intensity of the light source itself for use as a reference to the reagents' measurement.

It is a further object of the present invention to provide a monitor which will set off an alarm to warn the wearer if he reaches an exposure exceeding a predetermined level.

It is a further object of the present invention to provide a continuous monitor, capable of analyzing an integrated sample over an extended period of time and providing both the analyte concentration at any point during that time, and the average analyte concentration over the entire time period.

The device according to the present invention allows for real-time and/or time-history monitoring of a person's exposure to contaminants in the environment. An alarm will warn the person if he reaches an exposure exceeding a predetermined level, generally the eight hour OSHA permissible exposure level. This type of monitoring will facilitate compliance with federal (DOL, DOT and DHHS) and state standards.

In contrast to the device of the Gafford et al. patent, the device according to the present invention uses a dry material, on a dry substrate, thus there is no mix of a gel with the sensing material, resulting in an extended life of the device. The device according to the present invention uses only one light source and a reference detector to compensate for fluctuations in temperature, power, etc. Additionally, the need for optical filters is eliminated by the use of colored light emitting diodes.

According to a preferred embodiment of the present invention, the above objects are achieved by a thin film environmental monitor for monitoring a person's exposure to an analyte in an environment, comprising a portable casing for housing the monitor, a pump in the casing for obtaining an air sample, and a sensor in the casing for sensing the concentration of the analyte in the air sample obtained by the pump. The sensor includes an active film portion coated with a dry coating adapted to cause a chemical reaction with the analyte, and a reference film portion for transmitting incident light independently of the concentration of analyte in the air sample. The sensor generates an active signal representing the amount of light transmitted by the active film portion and a reference signal representing the amount of light transmitted by the reference film portion. A control circuit is provided in the casing for providing voltage to the sensor and for processing the active and reference signals from the sensor and producing an output signal representative of the concentration of the analyte in the air sample. Indicators are provided connected to the casing responsive to the control circuit for indicating the amount of analyte sensed based on the representative output signal.

Still other objects, features and attendant advantages of the present invention will become apparent to those skilled in the art from a reading of the following detailed description of the embodiments constructed in accordance therewith, taken in conjunction with the accompanying drawings.

BRIEF DESCRIPTION OF THE DRAWINGS

The invention of the present application will now be described in more detail with reference to the preferred embodiments of the device, given only by way of example, and with reference to the accompanying drawings, in which.

DETAILED DESCRIPTION OF THE PREFERRED EMBODIMENT

Figure 1:
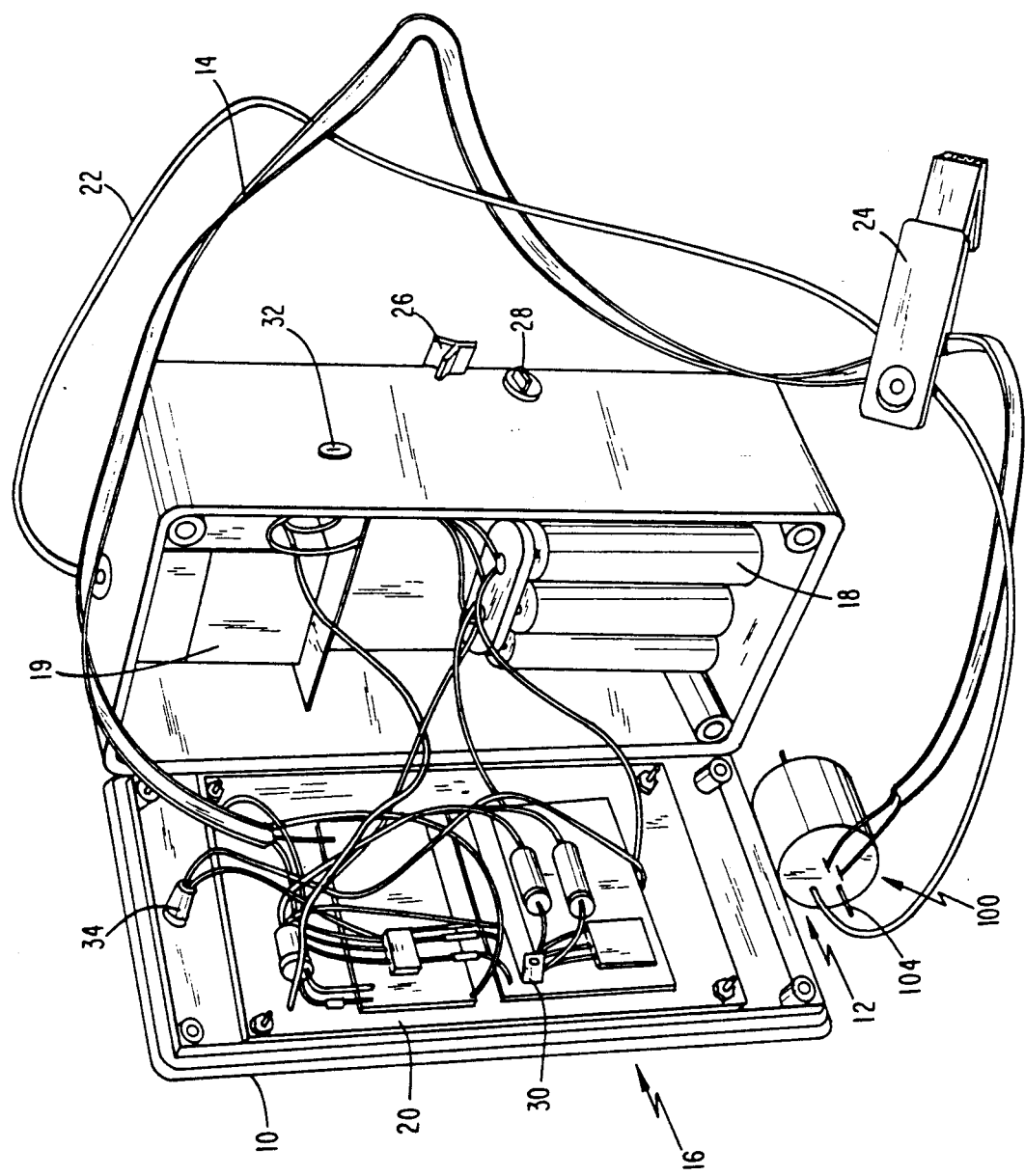
FIG. 1 is a perspective view of the opened thin film environmental monitor according to the present invention.

The sampler device 10 according to the present invention, shown in FIG. 1, consists of a breathing zone sensor 100 encased in a sensor housing 12 and connected by an electrical umbilical 14 to a belt-mounted processing unit 16 which provides power, signal processing, alarm, and air moving capabilities. The cylindrical sensor 100 weighs approximately 15 g, and is approximately 2 cm in diameter and 2.5 cm long. The belt unit 16 is approximately 450 g (including batteries) with dimensions 15 cm high, 8 cm wide, and 6 cm deep.

The principle of operation is a colorimetric reaction of contaminant with a translucent layer of reactant on a plastic substrate. The intensity of a color change reaction between the contaminant and the reactant is monitored by dual beam optics to compensate for temperature and power fluctuations. The color change is used to quantitate the amount of analyte according to the Beer-Lambert principle.

FIG. 1 is an overall perspective view of the opened sampler 10 according to the present invention including both the sensor 100 and the belt mounted processing unit 16 with its component structures. The battery pack 18, consisting of six rechargeable AA cells, supplies power to the air sampling pump 19 and the circuit board 20 mounted on the inside of the enclosure cover. The air sampling pump 19 pulls air through the sensor 100 by way of the air inlet 104 and the air flow umbilical 22. The circuit board 20 provides voltage to, and processes the signal from, the sensor 100 by way of the five conductor electrical umbilical 14. The collar clip 24 holds the sensor 100 in the desired location. Mounted on the back of the processing unit 16 is a belt clip (not shown) used to attach the device to the belt of the worker.

The function switch 26 determines the mode of operation of the device. It is moved from the first (off) position to the second (test) position in order to verify that the LED alarm 28 is working. In the third (set) position, the zero set potentiometer 30 (R3 in FIG. 3) is adjusted to calibrate the instrument, and the pump flow rate is adjusted using the pump flow adjust potentiometer 32 (not shown in FIG. 3). The device is then ready for the fourth position, the "run" mode.

An operational cycle would consist of inserting a set of reference and active films 108, 110 into the sensor 100 by inserting the guide pins 124 into guide holes 126 to properly align the film in the sensor, going through the steps outlined in the previous paragraph, and allowing the unit to sample in the "run" position for up to one work shift, or until the alarm light 28 comes on. At the end of a run, the voltage output would be read from the signal output jack 34, and compared with a calibration plot prepared previously using an identical film exposed to a known quantity of analyte via the sampler. Thus, the degree of exposure of the worker during each work period could easily be determined.

During instrument operation, the alarm light 28 (LED 2, FIG. 3B) would be activated if the battery dropped below a predetermined voltage, or if a high exposure was indicated by the signal from the sensor 100. Either of these conditions would be an indication to the wearer to leave the work area. Although the alarm light 28 is shown in FIG. 1 as consisting of one LED display which lights when either the battery is low or the exposure level to the contaminants is too high, it would be possible to have two separate LED displays. In this way, the worker would know immediately whether he has been exposed to high levels of contaminant or whether he simply needs new batteries. FIG. 3B includes two LED's used for display (LED's 2 & 3). Further, one or both of the alarms could have an audio alarm in addition to or in place of the LED display.

A signal output jack 34 is also placed on the cover of the processing unit 16. As noted above, this jack provides the connection for reading the instrument data output at the completion of a cycle, or for connection to a continuous data logging device which could also be worn on the worker's belt. This second option would provide a time history of the exposure.

Figure 2:
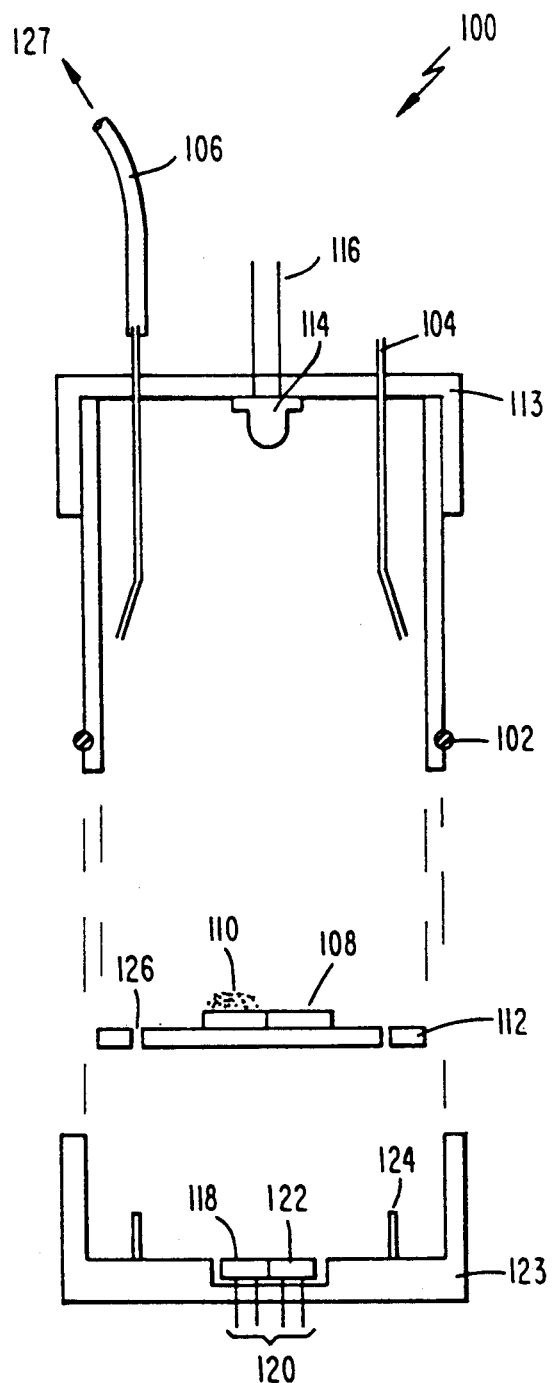
FIG. 2 is an exploded diagram of the sensor according to the present invention.

FIG. 2 is a diagram of the sensor 100 showing its component parts. The sensor 100 is made air-tight by means of an O-ring seal 102 to insure that the only air into the system is through the designated air inlet 104. This seal 102, the light traps of the air inlet 104 and the air outlet 106, and the matte black finish of the exterior render the sensor 100 light-tight. An air sample is pulled into the sensor 100 by the vacuum created when air is removed from the sensor via the air outlet 106 which is connected to the air sampling pump 18 in the belt unit 16 by the air flow umbilical 22.

The reference and active photocells 122 and 118 are disposed on the back face 123 of the sensor. Guide pins 124 extend perpendicularly from back face 123. Clear substrate 112, on which the reference and active films 108 and 110 are disposed, is provided with two guide holes 126. When the substrate 112 is inserted into the sensor, guide holes 126 mate with guide pins 124 to ensure accurate film alignment.

As the air sample containing the analyte of interest is drawn into the sensor 100, it flows past the reference and active films 108 and 110 supported on a clear substrate 112. The sample is allowed to react with the chemical coating on the active portion of the film which undergoes a color change, the intensity of which is proportional to the amount of analyte in the air (Beer-Lambert principle).

As the color intensity of the active film 110 increases, less light is transmitted from the light emitting diode (LED) 114 to the active photocell 118, the LED 114 being disposed an the front face 113 and connected to the power source in the processing unit by LED electrical leads 116. This results in a voltage change across the active photocell 118 which is transmitted to the circuit board 20 in the processing unit 16 by the electrical umbilical 14 connected at the photocell electrical leads 120.

The reference film 108 transmits incident light independently of concentration of analyte in the air sample. Any changes in voltage in the reference photocell 122 will, therefore, be a result of changes in conditions common to both the active and the reference photocells 118 and 122, such as temperature or input voltages. By measuring these changes with the reference photocell 122, compensation is made automatically at the circuit board 20, thereby making the output from the device independent of temperature and voltage fluctuations. This improves significantly the accuracy and sensitivity of the monitor.

The particular coating to be used on the active film depends on the analyte which is to be tested for by the monitor. For example, to detect the amount of mercury, a clear plastic film can be coated with small particles of copper iodide. To use the device for detecting ammonia, the Kodak Ektachem clinical slide can be used.

The circuit board 20 will now be described with reference to FIGS. 3A and 3B. Table I below is a legend associated with the operation and construction of the circuit shown in FIGS. 3A and 3B.

---

D14, D20, D24, D25, D26 - 1N4001
R6 = R7
SAT1 - Select for $V_{act}$ = +0.2 V
SAT2 - Select for alarm at $V_o$ = depends on film
SAT3 - Depends on film

---

In "SET" position, after 2 minute warmup with film in place, turn R3 Cw until LED2 comes "on". Then turn R3 CCW until LED2 just goes out.

TABLE I

Figure 3A:
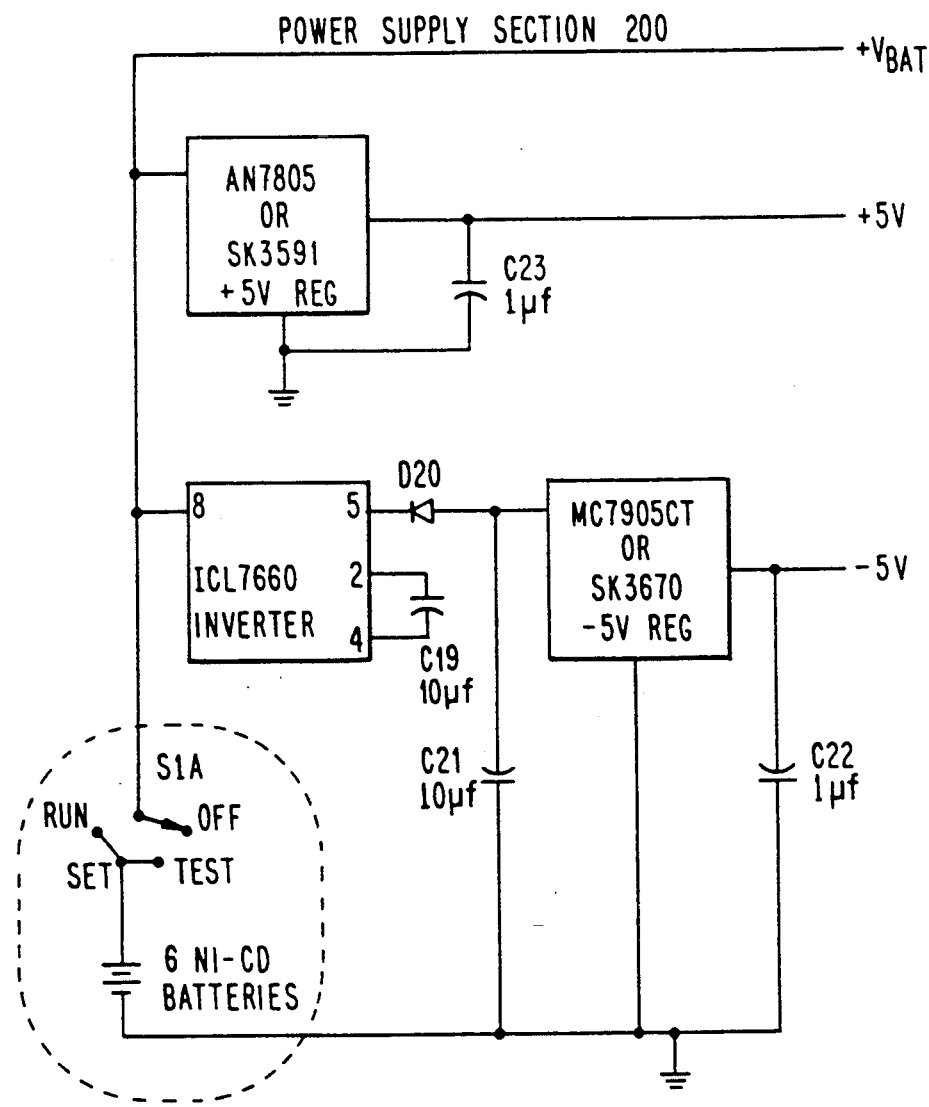
FIG. 3A is a schematic of the power supply section of the circuit board according to the present invention.
Figure 3B:
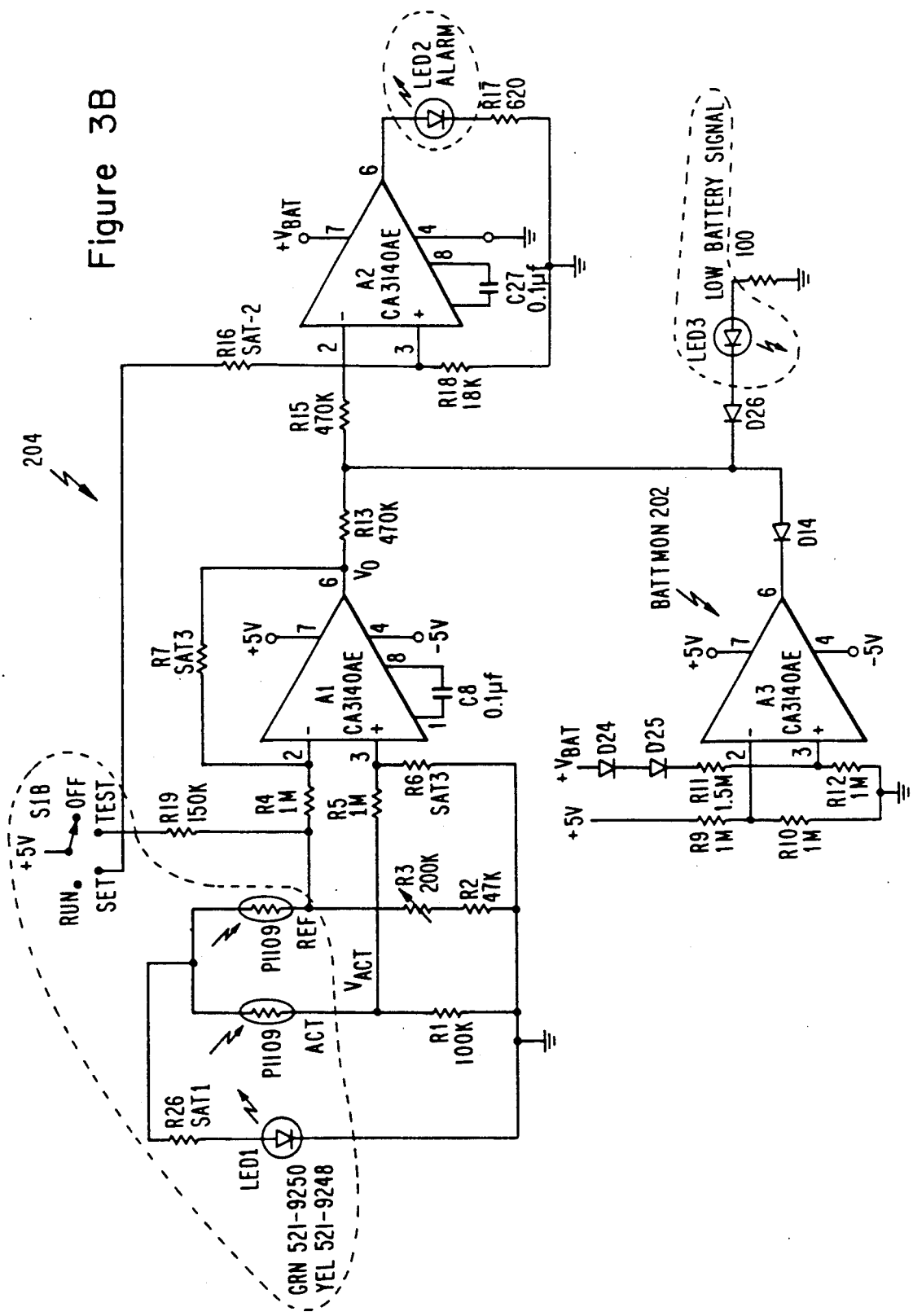
FIG. 3B is a schematic of the monitoring section of the circuit board according to the present invention.

FIG. 3A is a schematic of the power supply section 200. This section takes the battery voltage from the six nickel-cadmium batteries and provides unregulated battery voltage and regulated voltages of +5 volts and −5 volts to power the rest of the electronics.

The battery monitor section 202 (FIG. 3B) constantly monitors the battery voltage. If the battery voltage drops below +7 volts, both LED2 and LED3 will light.

The main section electronics 204 includes LED1, the active (ACT) and reference (REF) photocells, amplifiers A1 and A2, the switch S1B and the associated resistors, diodes and capacitors. LED 1 is used as the light source for the sensor. The operation of the system is as follows.

When switch S1 is set in the TEST position, the FUNCTION CHECK MODE is operational to test whether A1, A2 and LED2 are working. When the switch is in the "Function Check" mode, a voltage which is higher than normal is placed on inverting input of op-amp A1 via R19. This forces the output of A1 to go negative, which puts a negative voltage on the inverting input of A2. Since the non-inverting input of A2 has a positive voltage on it, the output of A2 will go to $+V_{BAT}$ and LED2 will turn on. This is a test for proper operation of the electronics which may be performed at anytime.

When switch S1 is in the "SET" position, the electronics are set to correct for slight variations in films. For the purpose of explaining circuit operation: the switch is in the SET position; R16 (SAT2) is 882 Kohms; and R6 and R7 (SAT3) are 1 Mohm. Thus, the voltage on the non-inverting input of A2 is +0.1 volts and the gain of A1 is one. With the switch in the SET mode, the film is inserted into the sensor and R3 is adjusted until LED2 (the alarm) just goes out. This happens when the voltage on the inverting input of A2 is +0.1 volts, i.e., the inverting input equals the non-inverting input.

The switch S1 is then turned to the RUN mode, removing the +0.1 volts source from the non-inverting input of A2 and replacing it with 0.0 volts. The +0.1 volts input is still on the inverting input. The instrument is now ready for operation. LED2 will not come on again until the voltage on the inverting input drops below 0.0 volts. This can occur via a signal from Al or from the Battery Monitor section 202 (A3). The output voltage of Al is now approximately +0.1 volts. The output voltage of A3 is positive but is blocked, by diode D14, from affecting A2.

When the switch S1 is set to the "RUN" position, the operation of the monitor begins. During the SET operation, the output of Al was set to approximately +0.1 volts. Since the gain of Al is one, this happened when the voltage differential between junction R3/R4 and was about −0.1 volts.

$$V_{R3/R4} - V_{R1/R5} = 0.1 \text{ volts}$$

Another way of looking at this is to say that the voltage differential between the ACTIVE and REFERENCE photocells is 0.1 volts.

$$V_{REF} - V_{ACT} = +0.1 \text{ volts}$$

This is the condition at the start of the RUN operation.

As the vapor of interest reacts with the coating on the active side of the sample film, the quantity of light which gets to the ACTIVE photocell decreases. The light may be red, yellow or green depending on the LED used to match the spectrum of the film. This causes the resistance of the ACTIVE photocell to increase. The coating on the reference side of the film remains the same color and the resistance of the REFERENCE photocell remains constant. Thus, the voltage at junction R5/RI drops and the voltage at junction R4/R3 remains constant. This causes the output of Al to decrease from +0.1 volts.

When the resistance of the active photocell increases further, the output voltage decreases further. When it drops below 0.0 volts, the output of A2 goes to $+V_{BAT}$, and the alarm LED2 is turned on.

The purpose of the REFERENCE photocell is to compensate for changes in the output of LED1, power supply voltages or temperature which may occur during operation. The use of the REFERENCE photocell significantly improves the accuracy and the sensitivity of the device.

Ammonia generated by a dynamic system was used to test 5 identical prototype devices in order to determine the consistency of the results obtained using the device. Four prototypes are identified as Units B through E. The fifth prototype, Unit A, was connected in series behind Unit C to estimate the efficiency of the reaction, and that data is presented separately.

Quantitative testing to date has been with ammonia in clean air. Levels of analyte were at the NIOSH recommended standard (for ammonia this is 35 ppm), and approximately half the recommended standard. In the data presented below, the four sensors were exposed to identical concentrations of ammonia connecting them to a common sampling manifold. The contaminant was generated using a permeation tube system as decieribed by Woodfin ("Gas and Vapor Generation Systems for Laboratories," NIOSH Technical Report, 8/84, DHHS (NIOSH) 84–113) with concentrations calculated from tube weight loss and air flow. The film used in this experiment was the Kodak ® Ektachem clinical chemistry slide.

Air was drawn from the sampling manifold through the sensors by a common vacuum source. Flow was regulated in each sensor by a limiting orifice placed in line between the sensor and the vacuum source. The flow rate through the sensors ranged from 0.16 and 0.70 mL per minute. All air flow rates were measured by moving film flow meters.

When testing for mercury, the OSHA "Acceptable Ceiling Concentration" is 0.1 ug/1 which is roughly 12 ppb. Because of this relatively low standard, much of the inventors' effort has gone into development of a film for transmitted light which is sensitive to mercury. Several color change schemes, film types and coating methods were investigated. The best combination found was to coat small particles of copper iodide onto a clear plastic film. Copper iodide will change color from white to orange when it reacts with mercury. This change initially increases then reduced he amount of light transmitted through the film to the sensor.

There are several problems with the film although it appears usable with some care. A drier in the sample line is needed to stabilize the humidity. Another problem is that some of the CuI coating can be removed by touching the film surface with a finger. Finally, only about 5% of the mercury in the sample stream reacts when it impinges on the copper iodide, so color change (sensitivity) is not a great as anticipated.

Figure 4:
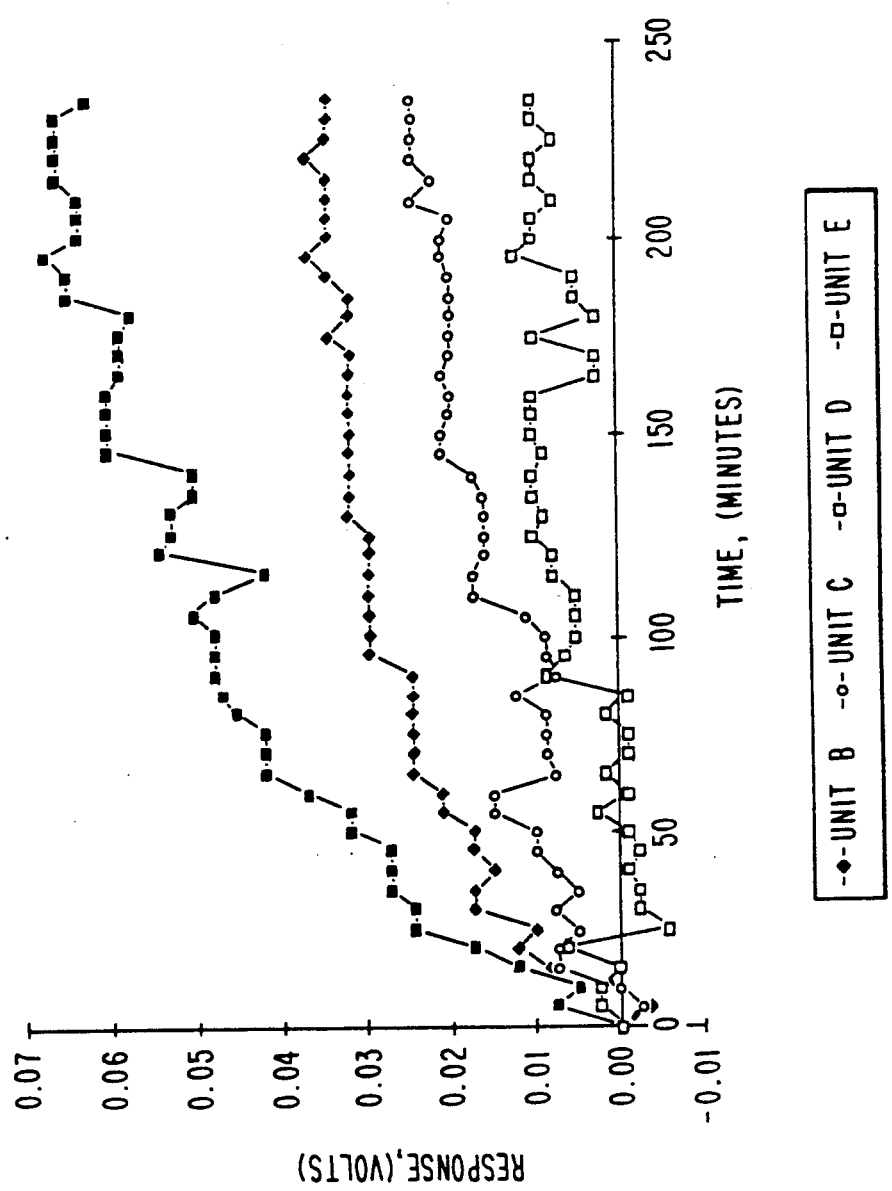
FIG. 4 is a graph showing zero drift with the ammonia sensitive film, i.e., the response to clean air as a function of time.

FIG. 4 shows the results of the four prototype devices with ammonia film subjected fro four hours to clean air. While this plot indicates that there is some response, the magnitude of the response is less than 70 mV for all four devices. This zero drift is acceptable relative to the 1 to 2 volt responses shown in the next figures.

Figure 5A:
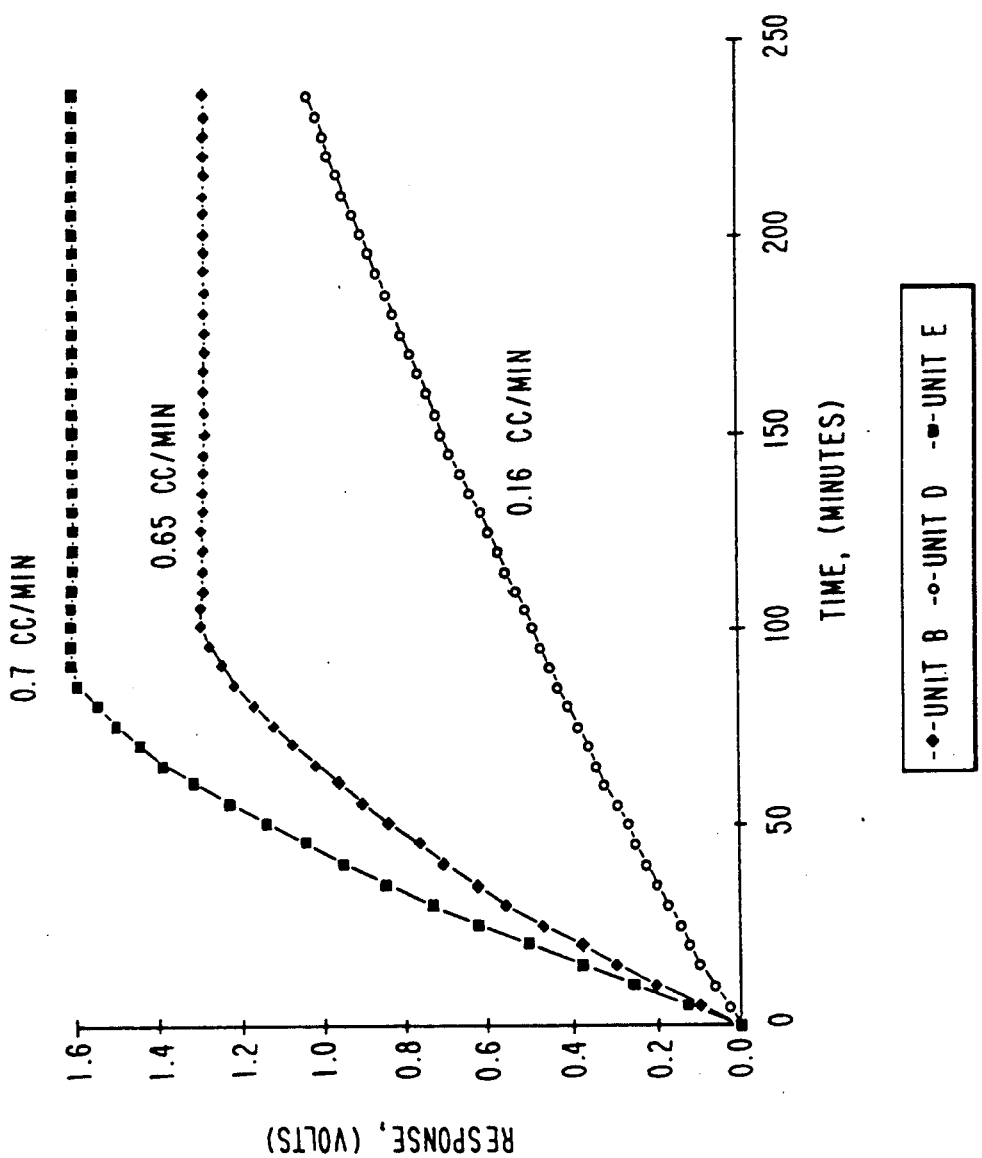
FIG. 5A is a graph of the saturation limit, i.e., response vs time at 35 ppm ammonia.

FIG. 5A shows the results of three devices subjected to a constant ammonia concentration of 35 ppm for four hours. (In this test, device C was aligned incorrectly, making that data invalid. It is therefore deleted from this figure.) There are two interesting points made by this plot. First, the sensors with the higher flow rates reach saturation first. It should be noted here that the magnitude of the response at saturation is related to both chemical and electrical parameters of the sensor. The electronic saturation voltage is determined by the bias setting of the individual sensor and can be extended somewhat (note Units B and E did not saturate at the same voltage). Chemical saturation (when no further color change s possible) is a function of flow rate, concentration and time. Extending the chemical saturation has not been pursued.

The second point indicated by this plot is that each sensor has a linear range of operation. While it may not be readily apparent from this plot, subsequent figures will show that this linear range is proportional to the flow rate times concentration, and therefore the total amount of ammonia to which the sensor is exposed.

The horizontal axis of FIG. 5A can be converted from units of time to units of ammonia volume as follows:

$$V_{(nL)} = t_{(minutes)} \cdot C_{(nL/mL)} \cdot f_{(mL/minute)}$$

Figure 5B:
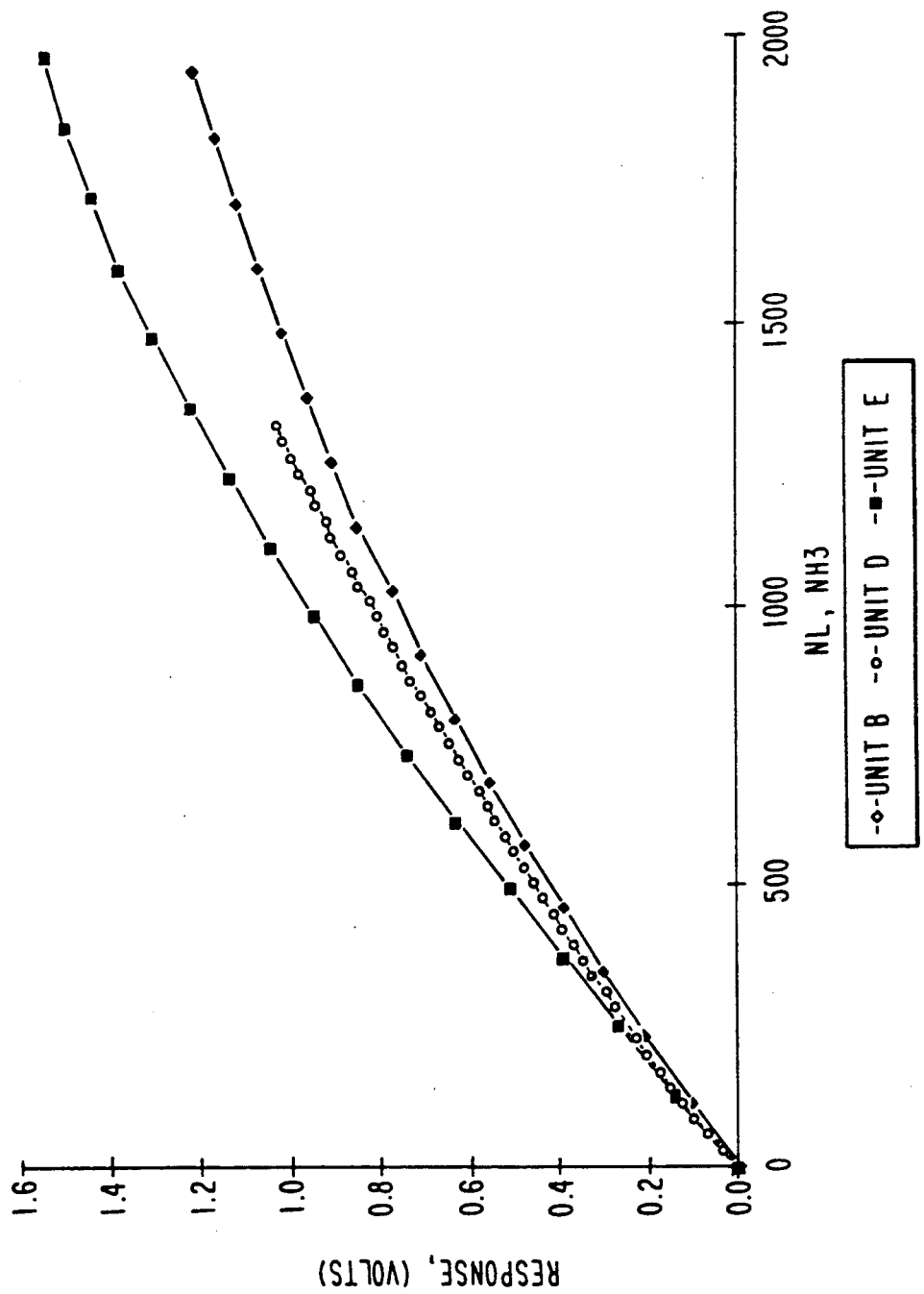
FIG. 5B is a graph of response vs volume of NH3.

-continued where  V = ammonia volume in nL
       t = time in minutes
       C = ammonia concentration in ppm
           (which is equivalent to nL/mL)
       f = flow rate in mL/minutes A transformed plot of the linear portion of FIG. 5A becomes FIG. 5B. This figure also shows the reproducibility between devices, although this is better illustrated by the next figure.

Figure 6:
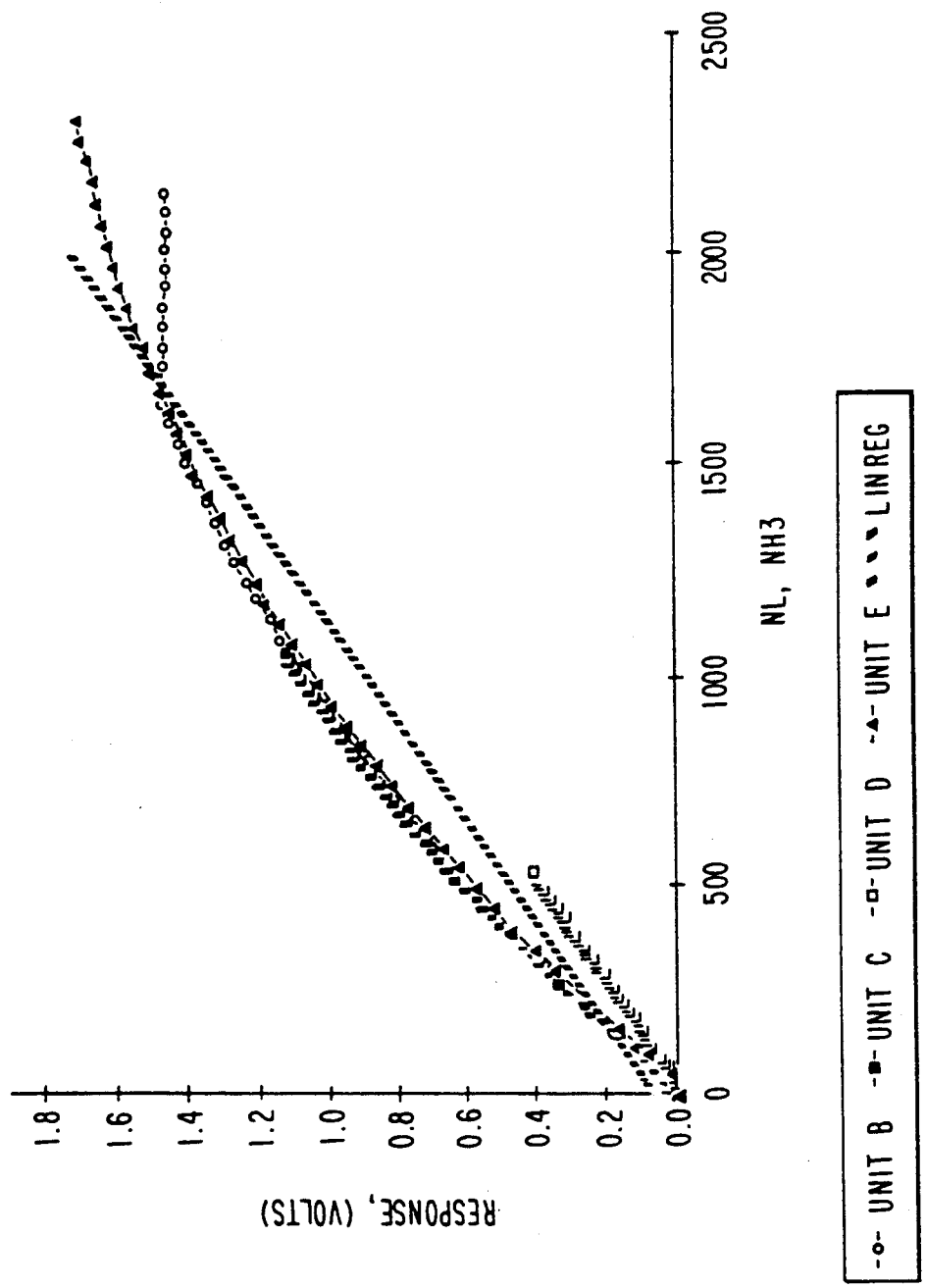
FIG. 6 is a graph of 35 ppm ammonia for 90 minutes, i.e., dose vs response for units B-E.

FIG. 6 shows all four sensors subjected to a constant 35 ppm for 90 minutes. Because of the difference in flow rates, all four are not subjected to the same total dose of ammonia. It is evident from this figure that Unit B has reached its saturation point prior to Unit E. The reason for this is the electronic saturation mentioned earlier. Excluding the data from Unit B past its saturation point, a linear regression on all four sets of data produces the indicated line with a correlation coefficient of 0.95. The slopes of the four separate lines, again including B, have a relative standard deviation of 17%.

Figure 7:
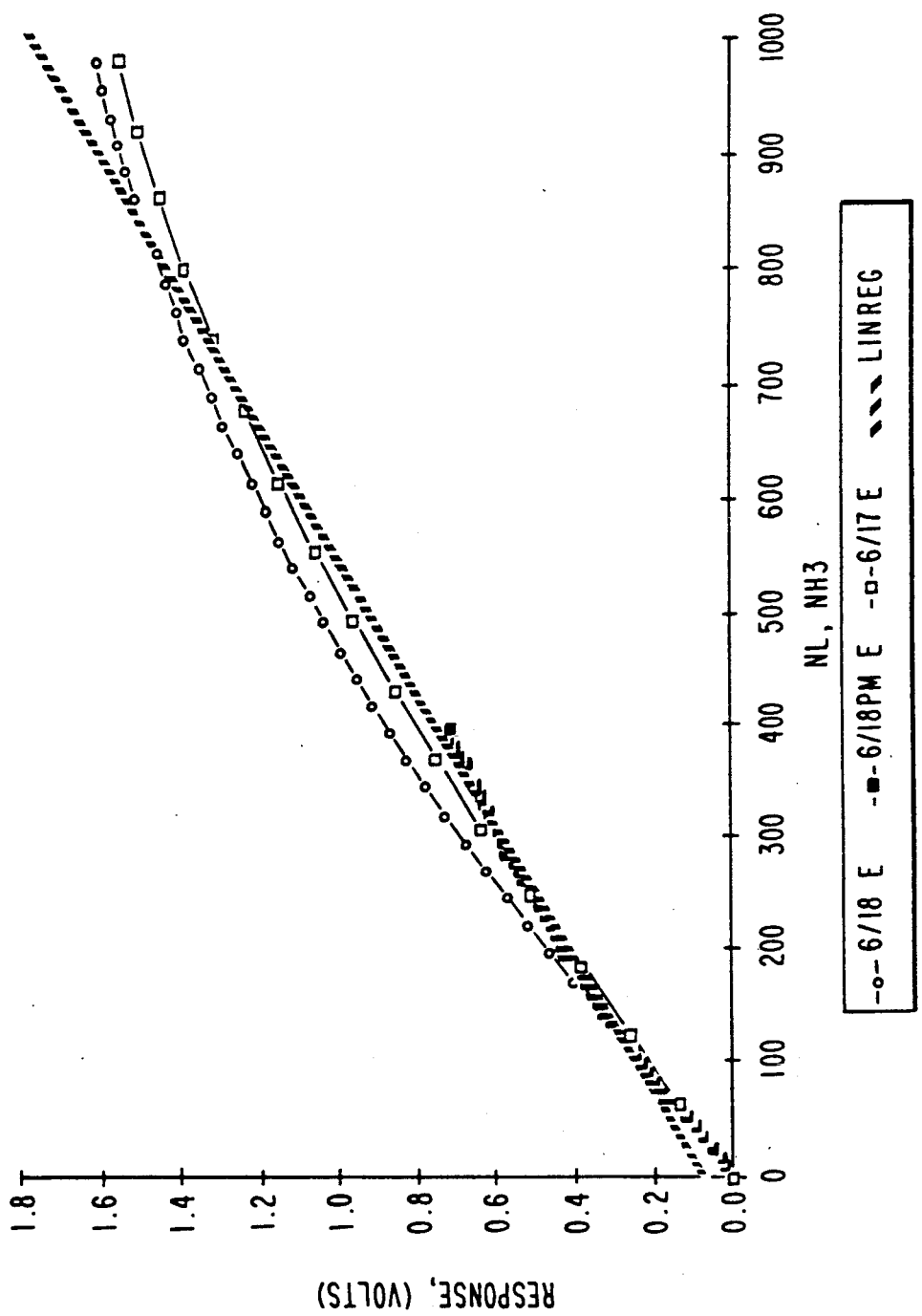
FIG. 7 is a graph of ammonia dose vs response for multiple runs of unit E.

The reproducibility within a unit is exemplified in FIG. 7. In three separate runs, Unit E was subjected to ammonia concentrations of 35, 35, and 12 ppm for plots identified as 6/17, 6/18 and 6/18 PM, respectively. Since the sensor's flow rate was the same for all three tests, the total dose to which it was exposed was less at the lower concentration. The correlation coefficient for the linear regression line of these data (again shown as a separate line) is 0.98. The relative standard deviation for the slopes of the separate lines is 6.4%.

Figure 8A:
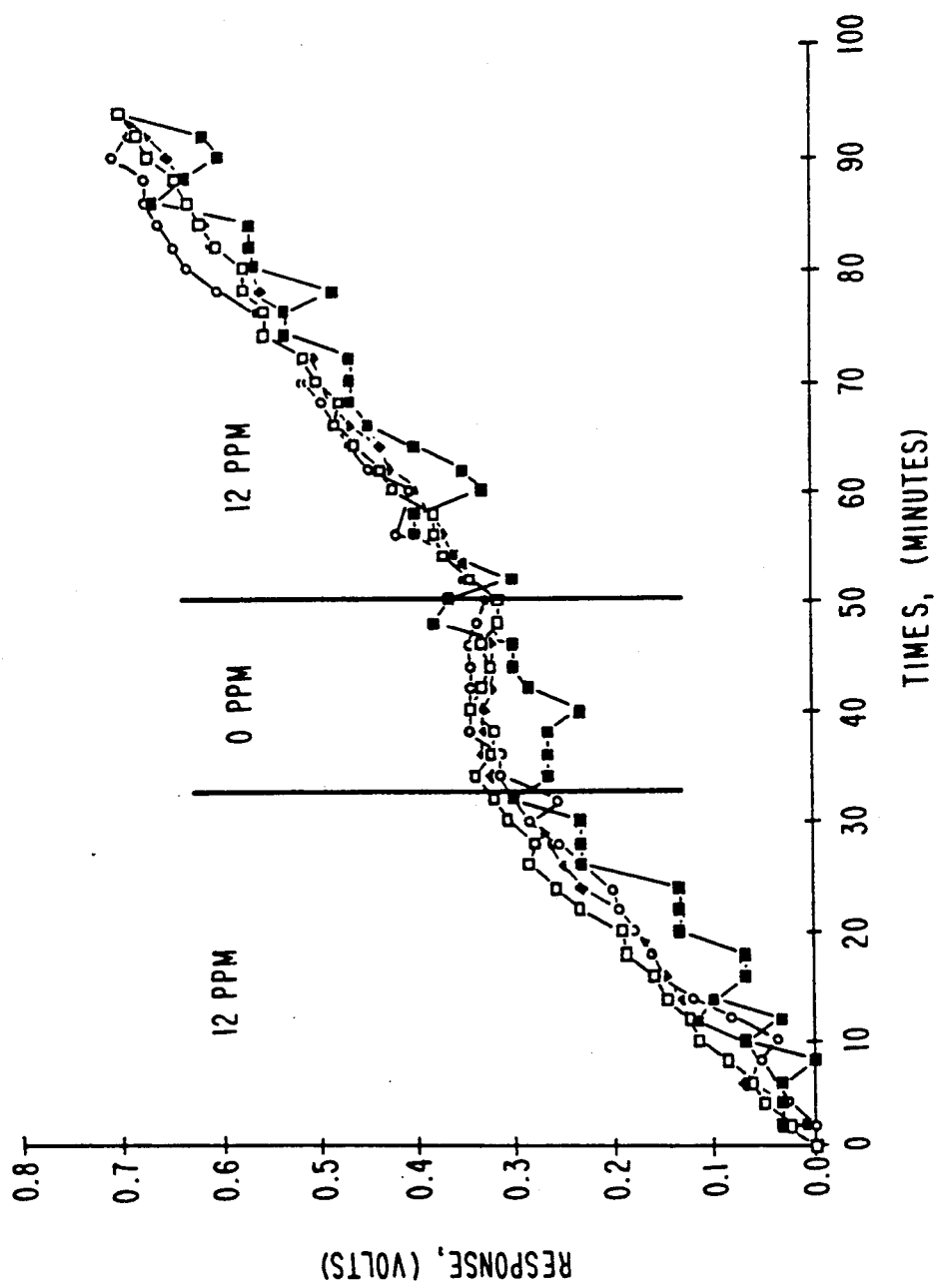
FIG. 8A is a graph of ammonia dose vs response, normalized, at varying conditions of units B-E.

The ability of the sensors to respond differently to different concentrations of analyte is shown in FIG. 8A. In this test, the four prototype devices were subjected to 12 ppm of ammonia for approximately 34 minutes, followed by 16 minutes in clean air, then the balance of the 90 minute run at 12 ppm. Results of this run have been normalized to a common value in order to compare the four units.

Figure 8B:
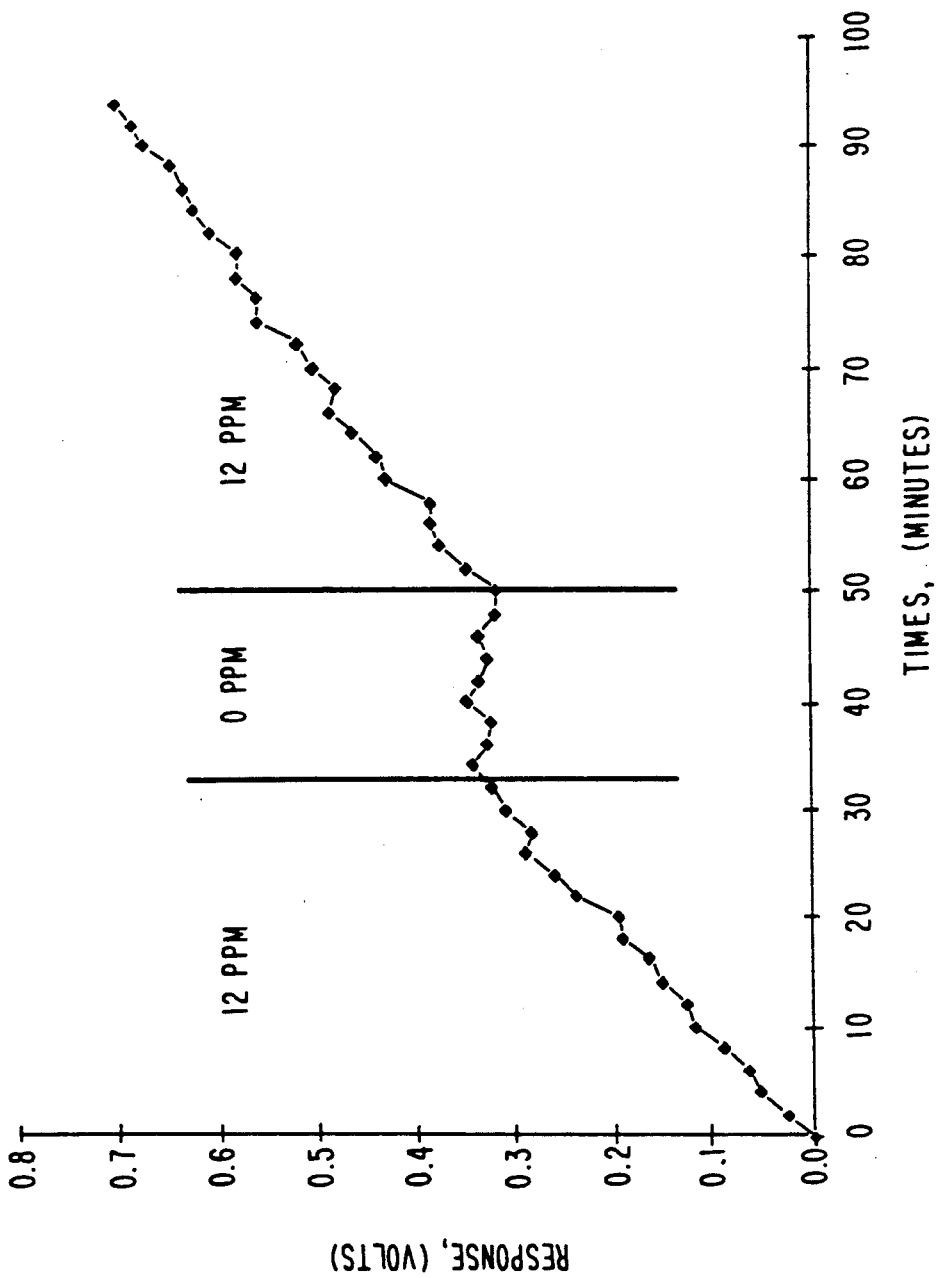
FIG. 8B is a graph of ammonia dose vs response of unit E at varying concentrations.

While this figure again shows the uniformity of response of the four devices, it is easier to illustrate the variation of response to concentration by selecting just one device and therefore having a less cluttered figure. FIG. 8B does this.

Figure 9:
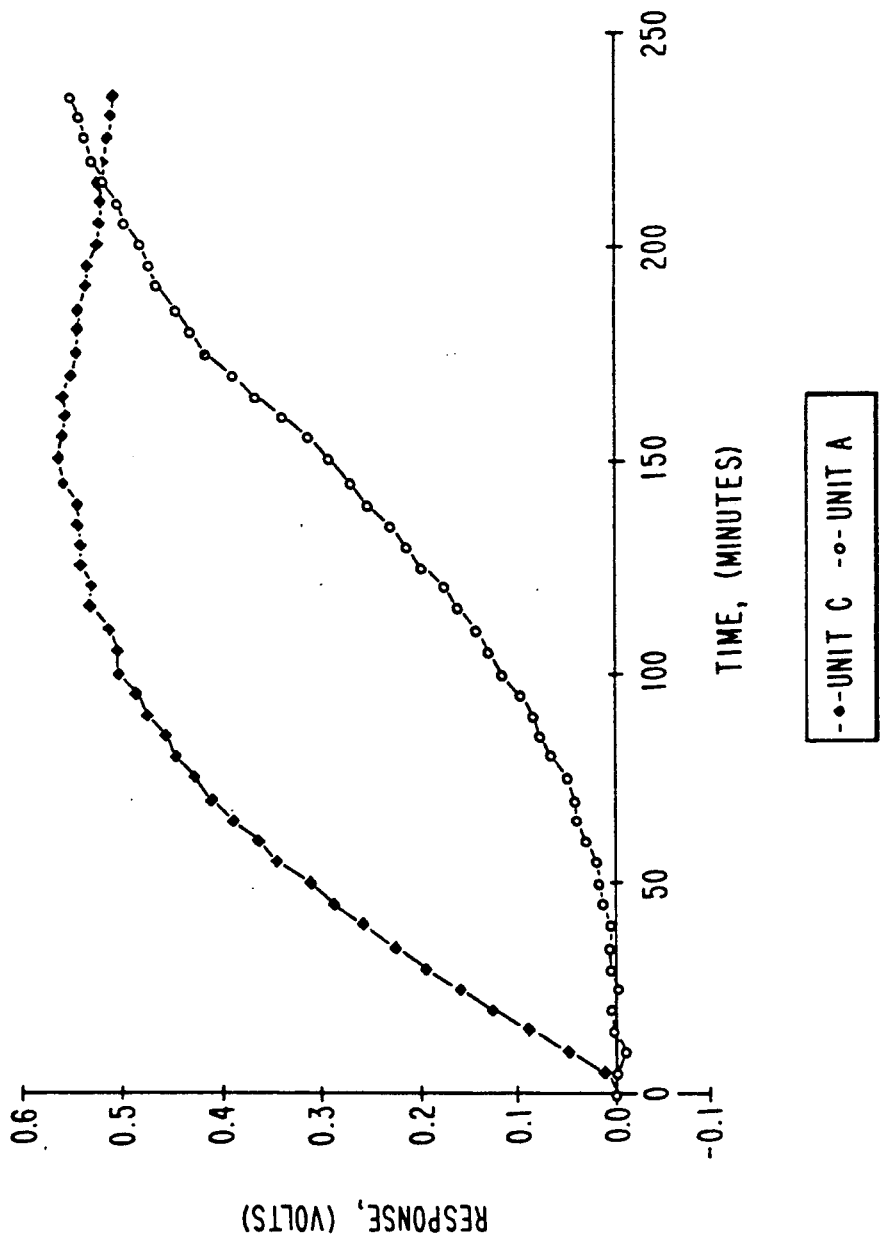
FIG. 9 is a graph of sensor efficiency, i.e., time vs response for sensors in series.

The final plot, FIG. 9, illustrates the efficiency of the reaction by plotting the two units which were connected in series. The experimental set-up was such that the contaminant air stream containing 35 ppm of ammonia was pulled first through Unit C, then through Unit A. Since the devices were in series, the flow rate through both was the same.

FIG. 9 indicates that at the beginning of the experimental period, most of the ammonia being drawn into the first sensor (C) was being reacted since little was being measured by the second (A). As the exposure continues, and reaction sites in "C" decrease, the efficiency of this sensor decreases, and the second detector begins to react.

Preliminary testing for interfering compounds indicates that strong acid and alkali have no noticeable effect on the color indicating layer. Some amines do appear to produce positive interference. As might be expected, the degree of interference seems to decrease as the amine goes from primary to secondary to tertiary. Interference also seems to decrease with increasing molecular weight within a group.

While some of the inventors' tests have been with films which operate based on chemical reactions which result in color changes because of the pH of the dye, there are many other chemical reactions which result in a color change not caused by changes in the pH of a dye. Some of the reactions the inventors are investigating include, but are not limited to, the reaction of mercury with copper iodide to produce an orange color; the reaction of carbon monoxide with iodine pentoxide (white) in the presence of selenium oxide and acid catalysts (white) to form iodine (brownish green); and the reaction of aldehyde vapor with chromic acid (orange) and sulfuric acid (white) to produce a brownish-green stain.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A thin film environmental monitor, comprising a portable casing;
   a monitor means for an analyte suspected of being present in an atmosphere in which the monitor is placed, the monitor means comprising
   sensor means for sensing the presence of the analyte in the atmosphere, the sensor means comprising (a) a portable housing; (b) a first conduit provided with first and second open ends for intake of a sample of the atmosphere through the first end, passage of the sample through the first conduit and disposal of the sample therefrom through the second end, wherein the first end of the first conduit is in communication with the atmosphere and he second end is positioned near first and second thin film means located in said housing, (c) said first and second thin film means for transmitting at least a fraction of any light incident thereon in the presence of the analyte in the sample and independent of its concentration therein, the first thin film means being coated with a dry composition for reacting with any analyte in the sample to thus interfere with the transmission of incident light by the first thin film means in a manner proportional to the concentration of analyte in the sample, (d) first and second photocell means spaced from the first and second thin film means in said housing and placed in a path of the transmitted light beam to generate first and second electric signals that are proportional to the light transmitted by the first and second thin film means in response to the incident light;
   electric pump means in said casing for continuously providing the sample to the sensor means at a predetermine flow rate, the pump means being operatively connected to the sensor means by a second conduit provided with first and second ends, the first end of the second conduit being placed in the sensor means and the second end of the second conduit connected to the pump means;

control means in said casing for processing the first and second electric signals, for generating an output signal that is proportional to the concentration of anlyte in the sample, and for controlling with the pup means the flow rate of the sample flowing through the sensor means, the control means being electrically connected to the sensor means, the pump means, an indicator means, an on-off switch means, and a source of power, said source of power located in said casing;

said indicator means for continuously indicating the output signal and the concentration of analyte present in the atmosphere, the indicator means being connected to the casing;

light source means for providing a beam of incident light the first and second film means; and said on-off switch means for the pump means; wherein when the control means is electrically connected to the power source and the switch mean is in the "on" position, the sample is pumped into the sensor means and reacts with said dry composition coated on said first film means, the first and second electric signals and the output signal are generated, and the concentration of analyte in the sample is indicated by the indicator means.

2. The tin film environmental monitor of claim 1, wherein the control means comprises processing means for generating the output signal from the first and second electric signals received from the sensor means; and activation means for activating the indicator means to receive the output signal produced by the processing means.

3. The thin film environmental monitor of claim 2, wherein
the indicator means comprises at least one light emitting diode which lights up in response to the activation means when the output signal reaches a predetermined value.

4. The thin film environmental monitor of claim 3, further comprising
at least one battery means for supplying power to he pump means and to the control means; and wherein the indicator means comprises at least one light emitting diode which lights up when the at least one battery means drops below a predetermined voltage.

5. The thin film environmental monitor of claim 2, wherein
the indicator means comprises means for recording the output signal.

6. The thin film environmental monitor of claim 1, wherein the on-off switch means comprises
mode switching means for switching the operational state of the monitor between a test mode, a set mode, and a run mode.

7. The thin film environmental monitor of claim 6, wherein
the control means comprises test means for testing whether the indicator means is operational when the mode switching means is in the test mode.

8. The thin film environmental monitor of claim 7, wherein the control means comprises set means for setting the control means to correct for slight variations in the first and second thin film means used when the mode switching is in the set mode.

9. The thin film environmental monitor of claim 8, wherein
the control means comprises run means for setting the monitor for sampling operations when the mode switching means is in the run mode.

10. The thin film environmental monitor of claim 1, further comprising
attachment means for attaching said casing to an article of clothing.

11. The thin film environmental monitor of claim 1, further comprising
an air flow umbilical cord to carry the sample of the atmosphere fro the sensor means to said pump means.

12. A sensor for sensing the concentration of an analyte in a sample from an atmosphere obtained by an electric pump means, the sensor comprising
sensor means for sensing the presence of the analyte in the atmosphere, the senor means comprising (a) a portable housing; (b) a first conduit provided with first and second open ends for intake of a sample of the atmosphere through the first end, passage of the sample through the first conduit and disposal of the sample therefrom through these contend, wherein the first bend of the first conduit is in communication with the atmosphere and the second end is positioned near first and second thin film means located int said housing, (c) said first and second thin film means for transmitting at least a fraction of any light incident thereon in the presence of the analyte in the sample and independent of its concentration therein, the first thin film means being coated with a dry composition of or creating with any analyte in the sample to thus interfere with the transmission of incident light by the first thin film means in a manner proportional to the concentration of analyte in the sample, (d) first and second photocell means spaced from the first and second thin film means in said housing and placed in a path of the transmitted light beam to generate first and second electric signals that are proportional to the light transmitted by the first and second thin film means in response to the incident light; (e) wherein said portable housing further comprises a back face on said housing on which the first and second photocell means are disposed; at least one guide pin means extending perpendicularly from the back face; and a clear substrate to which the first and second thin film ends are attached, the clear substrate comprising at least one guide hole means for mating with the at least one guide pin means when the substrate is inserted into the sensor means or ensuring accurate alignment of the first and second thin film means.

13. The sensor of claim 12, further comprising
a front face on said housing on which a light source is disposed, said light source providing a beam of incident light to the first and second thin film means, he front face being at an opposite end of the sensor from the back fa e.

14. A monitor, comprising
at least one sensor of claim 12;
a portable casing;

electric pump means in said casing for continuously providing the sample to the sensor at a predetermined flow rate, the pump means being operatively connected to the sensor means by a second conduit provided with first and second ends, the first end of the second conduit being placed in the sensor means and the second end of the second conduit connected to the pump means;

control means in said casing for processing the first and second electric signals, for generating an output signal that is proportional to the concentration of analyte in the sample, and for controlling with the pump means of the flow rate of the sample flowing through eh sensor means, the control means being electrically connected to the sensor means, the pump means, an indicator means, an on-off switch means, and a source of power, said source of power located in the cassing;

said indicator means for continuously indicating the output signal and the concentration of analyte present in the atmosphere, the indicator mean being connected to the casing;

light source means for providing a beam of incident light to the first and second thin film means; and said on-off switch mean for the pump means, wherein when the control means is electrically connected to the power source and the switch means is in the "on" position, the sample is pumped into the sensor means and reacts with said dry composition coated on said first thin film means, the first and second electric signals and the output signal are generated, and the concentration of analyte in the sample is indicated by the indicator means.

* * * * *